US010675334B2

(12) United States Patent
Taylor

(10) Patent No.: US 10,675,334 B2
(45) Date of Patent: Jun. 9, 2020

(54) MATRIX GEL

(71) Applicant: DE MONTFORT UNIVERSITY, Leicester, Leicestershire (GB)

(72) Inventor: Margaret Joan Taylor, Leicester (GB)

(73) Assignee: De Montfort University, Leicester, Leicestershire (GB)

( * ) Notice: Subject to any disclaimer, the term of this patent is extended or adjusted under 35 U.S.C. 154(b) by 0 days.

(21) Appl. No.: 15/042,629

(22) Filed: Feb. 12, 2016

(65) Prior Publication Data

US 2017/0007676 A1      Jan. 12, 2017

Related U.S. Application Data

(63) Continuation of application No. PCT/GB2014/052054, filed on Jul. 7, 2014.

(30) Foreign Application Priority Data

Aug. 15, 2013   (GB) .................................. 1314640.2

(51) Int. Cl.
*A61K 38/28* (2006.01)
*A61K 47/36* (2006.01)
*A61K 9/06* (2006.01)
*A61K 47/42* (2017.01)

(52) U.S. Cl.
CPC .............. *A61K 38/28* (2013.01); *A61K 9/06* (2013.01); *A61K 47/36* (2013.01); *A61K 47/42* (2013.01)

(58) Field of Classification Search
CPC ........ A61K 47/36; A61K 47/42; A61K 38/28; A61K 9/06; A61K 47/61; A61K 47/6425; A61K 47/6903; A61K 9/5161; A61K 9/5192; A61K 9/0004; A61K 9/0024; A61K 47/32; A61K 9/0014; A61K 9/205; A61K 9/2063; A61K 38/00; A61K 47/48276; A61K 47/48784; A61K 47/641; A61K 47/6415
See application file for complete search history.

(56) References Cited

U.S. PATENT DOCUMENTS

2016/0158145 A1    6/2016   Taylor
2017/0007676 A1    1/2017   Taylor

FOREIGN PATENT DOCUMENTS

| DE | 4039468 A1 | 6/1992 | |
|---|---|---|---|
| GB | WO03/006993 A2 * | 1/2003 | ........... G01N 33/543 |
| WO | 9313803 A1 | 7/1993 | |
| WO | 199316803 A1 | 9/1993 | |
| WO | 199501186 A1 | 1/1995 | |
| WO | 2003006993 A2 | 1/2003 | |
| WO | 2008112190 A1 | 9/2008 | |

OTHER PUBLICATIONS

Tanna, et al. "Glucose-responsive UV polymerised dextran-concanavalin A acrylic derivatised mixtures for closed-loop insulin delivery", Biomaterials, 27: 1586-1597. (Year: 2006).*
Tanna et al., "A Covalently Stabilised Glucose Responsive Gel Formation with a Carbopol Carrier", journal of Drug Targeting, 10(5): 411-418. (Year: 2002).*
Higuchi, T., "Mechanism of sustained-action medication. Theoretical analysis of rate of release of solid drugs dispersed in solid matrices," Journal of Pharmaceutical Sciences, 52(12):1145-1149, 1963.
Hartman, "Insulin Analogs: Impact on Treatment Success, Satisfaction, Quality of Life, and Adherence", Clinical Medicine and Research, 6(2):54-67, 2008.
Korolkovas, et al., "Theoretical Aspects of Drug Action", Essentials of Medicinal and Research, 44-81, 1976.
Andersson, "Molecular imprinting: developments and applications in the analytical chemistry field", Journal of Chromatography B, 745(1):3-13, 2000.
Bruggemann, et al., "New Configurations and applications of molecularly imprinted polymers", J. Chromatography A., 889(102):15-24, 2000.
Haupt, et al., "Plastic antibodies: developments and applications", Tibtech,16(11):468-475, 1998.
Lis, et al., "The Biochemistry of Plant Lectins (Phytohemagglutinins)", Annual Review of Biochemistry, 42:541-574, 1973.
Goldstein, et al., "The Lectins:Carbohydrate-Binding Proteins of Plants and Animals", Adv. in Carbonhydrate Chemistry and Biochemistry, Tipson and Horton eds., 35:127-341. 1978.
Miyake, et al., "Characteristics of Anti-testosterone Antisera Produced by Bovine Serum Albumin Conjugates of 15α- and 15β-Carboxymethyltestosterone: Use of [125I]Iodinated Tracers" Chem Pharm Bull, 38(4):951-955, 1990.
Kussie, et al., "Analysis of the Binding Site Architecture of Monoclonal Antibodies to Morphine by Using Competitive Ligand Binding and Molecular Modeling", The Journal of Immunology, 146(12):4248-4257, 1991.
Carnali, et al., "The Use of dilute solution viscometry to characterize the network properties of carbopol microgels", Colloid Polymer Sci., 270:183-193, 1992.
Fischel-Ghodsian, et al., "Analysis of Drug Release Kinetics from Degradable Polymeric Devices", Journal of Drug Targeting, (1):51-57, 1993.

(Continued)

*Primary Examiner* — Audrea B Coniglio
(74) *Attorney, Agent, or Firm* — Elmore Patent Group, P.C.; Mahreen Hoda; Carolyn Elmore

(57) ABSTRACT

The present invention relates to a gel having a three dimensional matrix structure and a drug in the form of a solid contained within the three dimensional matrix. Gels of the invention are preferably for implantation into a patient. Storing the drug as a solid within the gel means that the drug density is high in those areas of the gel which contain solid drug. The high drug density means that a larger amount of drug can be stored in a gel of a given size relative to the amount of drug that can be stored as individual molecules. The large deposit of solid drug means that the gel can sustain release of the drug for an extended period of time. This is advantageous because it minimises the frequency of replacement or replenishment of the implanted gel, thereby minimising discomfort and inconvenience to the patient.

24 Claims, 4 Drawing Sheets

Specification includes a Sequence Listing.

(56) References Cited

OTHER PUBLICATIONS

Brange, "Galenics of Insulin: The Physico-Chemical and Pharmaceutical Aspects of Insulin and Insulin Preparations",1-103:1987.

Kim, et al., "Modulated insulin delivery from glucose-sensitive hydrogel dosage forms," Journal of Controlled Release, 77:39-47, 2001.

Tanna, et al., "Glucose-responsive UV polymerised dextran-concanavalin A acrylic derivatised mixtures for closed-loop insulin delivery", Biomaterials, 27:1586-1597, 2006.

Tanna, et al., "Covalent coupling of concanavalin A to a Carbopol 934P and 941P carrier in glucose-sensitive gels for delivery of insulin", Journal of Pharmacy and Pharmacology, 54:1461-1469, 2002.

Tanna, et al., "A Covalently Stabilised Glucose Responsive Gel Formation with a Carbopol Carrier", Journal of Drug Targeting, 10(5):411-418, 2002.

Moravej, et al., Biodegradable Metals for Cardiovascular Stent Application: Interests and New Opportunities, Int. J. Mol. Sci., 12:4250-4270, 2011.

Taylor, et al., "In Vivo Study of a Polymeric Glucose-Sensitive Insulin Delivery System Using a Rat Model," Journal of Pharmaceutical Sciences, 99(10):4215-4227, 2010.

Tanna, et al., "The effect of degree of acrylic derivatisation on dextran and concanavalin A gluclose-responsive materials for closed-loop insulin delivery," Biomaterials, 27(25):4498-4507, 2006.

Taylor, et al., Glucose-sensitive gel rheology of dextran-concanavalin A mixtures suitable for self-regulating insulin delivery, Pharmaceutical Development and Technology, 15(1):80-88, 2010.

Zurich Artificial Pancreas, retrieved from the internet:URL:https://web.archive.org/web/20121227083918/http://www.renfrewgroup.com/pancreas, retrieved Aug. 26, 2014.

Crepy, "Synthesis of Cellulose Fatty Esters as Plastics-Influence of the Degree of Substitution and the Fatty Chain Length on Mechanical Properties," ChemSusChem, 2(2):165-170, 2009.

* cited by examiner

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens
<220> FEATURE:
<221> NAME/KEY: misc_feature
<223> OTHER INFORMATION: Insulin A-Chain

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens
<220> FEATURE:
<221> NAME/KEY: misc_feature
<223> OTHER INFORMATION: Insulin B-Chain

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Tyr Pro Lys Thr
            20                  25                  30
```

MATRIX GEL

RELATED APPLICATION

This application is a continuation of International Application No. PCT/GB2014/052054, which designated the United States and was filed on Jul. 7, 2014, published in English. This application claims priority under 35 U.S.C. § 119 or 365 to Great Britain, Application No. 1314640.2, filed Aug. 15, 2013. The entire teachings of the above applications are incorporated herein by reference.

The present invention relates to gel compositions which comprise gel forming moieties which bind to one another to form a gel. The binding of the gel forming moieties is dependent on the level of an analyte and the gel composition has a drug therein that is released in response to the analyte.

WO 03/006993 discloses a gel which, in one embodiment, comprises dextran and concanavalin A (ConA). Terminal glucose residues of dextran bind to ConA, resulting in the formation of a high viscosity gel. Reversal of this binding occurs when free glucose competes with the dextran glucose residues for binding to ConA, such that the gel loses viscosity. Thus, the gel is sensitive to the amount of free glucose with which it is brought into contact. As such, the gel can be used as a drug delivery system using an anti-hyperglycaemic drug such as insulin. In normal levels of glucose, dextran binds ConA and the gel can be used as a barrier to limit the release of insulin from a reservoir. However, when the level of glucose rises, the degree of binding falls allowing insulin to be released from the reservoir at an increased rate. In a physiological situation, the release of insulin will result in the level of glucose falling which in turn will cause the degree of binding to increase, thereby decreasing the rate of insulin release. Thus, the drug delivery system forms a "closed loop" system which mimics the activity of a normally-functioning pancreas, with insulin being released when required (when glucose causes the gel to undergo gel-sol transition) and retained when not required (when the lack of glucose causes the gel to undergo sol-gel transition).

There is an inherent risk associated with such a drug delivery system which stems from the fact that the drug is often stored in a large volume and/or at a high concentration in a reservoir located in the body of a patient. A large volume/high concentration may be preferable as this maintains the diffusion gradient and the effective dose rate and minimises the refill frequency necessary to maintain effective drug delivery, thereby limiting the discomfort and disruption to the patient associated with such refills. However, a structural failure or puncture of such a reservoir could result in the release of an unsafe or even fatal dose of the drug into the body of the patient.

WO 93/16803 and WO 95/01186 disclose a delivery system for delivering a drug for the treatment of a condition. Individual drug molecules are trapped within a biocompatible matrix which is sensitive to a physiological substance. The physiological substance causes a conformational change in the matrix allowing release of the drug.

In a first aspect, the invention provides a gel comprising first and second gel forming moieties which bind reversibly to one another to form a three dimensional matrix, said binding being sensitive to the level of an analyte, and a drug in the form of a solid contained in the three dimensional matrix.

The present invention provides an improvement over the delivery systems disclosed in WO 93/16803 and WO 95/01186. For example, storing the drug as a solid means that the drug density is increased in those areas of the gel which contain solid drug. In the context of the invention, "drug density" means the number of molecules of drug per unit volume. The increased drug density means that a larger amount of drug can be stored in a gel of a given size relative to the amount of drug that can be stored as individual molecules i.e. the size of the gel does not have to be increased in order to store a greater amount of drug. This is advantageous because gels of the invention may be implanted into a patient which may impose limitations on the dimensions of the gel.

The gel may contain a single mass of solid drug or may contain a plurality of discrete solid masses. The solid drug may be in the form of particles. The particles may have an average diameter of about 0.01 μm to about 2000 μm, about 0.1 μm to about 1750 μm, about 0.5 μm to about 1500 μm, about 0.75 μm to about 1250 μm, about 1 μm to about 1000 μm, about 1 μm to about 250 μm, about 250 μm to about 500 μm, about 500 μm to about 750 μm or about 750 μm to about 1000 μm. Such particles may have an average diameter of about 1 μm, about 10 μm, about 20 μm, about 30 μm, about 40 μm, about 50 μm, about 60 μm, about 70 μm, about 80 μm, about 90 μm about 100 μm, about 200 μm, about 300 μm, about 400 μm, about 500 μm, about 600 μm, about 700 μm, about 800 μm, about 900 μm or about 1000 μm. The solid drug or particles of the solid drug may be substantially evenly dispersed throughout the three dimensional matrix structure of the gel.

The large deposit of solid drug means that the gel can sustain release for a longer period of time without being replenished. If the gel is implanted into a patient to deliver a drug, this is highly significant as it minimises the discomfort and inconvenience which may be experienced by the patient when the gel is replenished or replaced. Unexpectedly, the inventor found that even though the drug is stored as a solid within the three dimensional matrix structure of the gel, the gel maintains sensitivity to the analyte. Also surprising was the finding that the controlled release of the drug in response to the analyte is comparable to gel-drug systems in which the drug is stored in solution, either in a reservoir or as individual molecules trapped in the gel. The possible reasons for this are discussed below. This means that a predictable output from the gel and thus a predictable blood level of the drug can be achieved when the gel is used to deliver the drug to a subject. In addition, the gel of the present invention has the advantage that there is no reservoir of drug in solution that can be released in the event of a puncture or structural failure. The risk of a patient who has a gel of the invention implanted in their body accidentally receiving an unsafe dose of drug is therefore greatly reduced.

The analyte-sensitive gel of the invention can control the rate of release of any drug which is present in solid form within the gel, the rate of release being controlled by (i) the concentration of the analyte in the environment in which the gel is located (because the gel is sensitive to the analyte), (ii) the concentration gradient of the drug, (iii) the surface area and thickness of the rate determining membrane i.e. the gel, and (iv) the diffusion coefficient. The diffusion coefficient is inversely related to the viscosity of the gel by the Stokes-Einstein equation. The rate of release can be expressed using the equation: $dM/dt = D \cdot A \cdot dc/dx$, where D is the diffusion coefficient, x is the thickness of the gel, A is area of the gel and c is the concentration of the drug (dc/dx is the concentration gradient).

The mechanism of release can be summarised as follows. The drug is stored in the gel in the form of a solid, which is in dynamic equilibrium with dissolved drug. As discussed above, the gel becomes less viscous in response to an increased concentration of the analyte. This is because the analyte competes with the second moiety to bind the first moiety and therefore as the concentration of analyte increases, the three dimensional structure of the gel progressively dismantles and hence becomes less viscous. The reduction in viscosity allows the dissolved drug to diffuse away from the gel to a site of action, which in turn causes dissolution of the solid drug to restore equilibrium between solid and dissolved forms of the drug. The freeing up of water bound in the structure of the gel is also thought to contribute to this effect. As the concentration of analyte increases, the rate at which the drug is released from the gel is increased. Conversely, a decrease in the concentration of analyte causes the gel to become more viscous as its three dimensional structure is restored, thereby reducing the rate at which the drug is released from the gel. The output of drug from the gel relies on the release of drug that is dissolved in the gel and the further dissolution of solid material to maintain the equilibrium between dissolved drug and solid drug in the gel.

As mentioned above, output or delivery of a drug stored in solid form contained within a three dimensional matrix structure of an analyte sensitive gel (a "matrix design") was found to be comparable to output/delivery of a drug which is not stored within the three dimensional matrix structure of a gel but stored in solution, for example in a reservoir "gated" by an analyte sensitive gel (a "reservoir design"). This was not expected because of the known differences in delivery between reservoir systems and matrix systems.

Where a drug in solution, such as insulin, is released from a reservoir, the output is almost linear if the concentration of drug remains very high compared with the medium into which the drug is delivered. This means that the output is independent of time. This result is known as zero order delivery and is much sought after because for many drugs and their formulations, zero order delivery fosters a predictable and constant blood level. In practice, the rate will fall off only very slowly if the concentration of drug in the reservoir is high and will continue predictably if the concentration of the drug in the medium is zero or low (as when insulin is rapidly removed from the delivery site by uptake or metabolism). Systems containing un-dissolved drug in a saturated solution will maintain the driving force and linearity referred to here until the replacement fails as the supply is eventually exhausted. This is true for solids that have normal solubility characteristics; but those, like insulin, that depend on additives like phenol, zinc and hydrogen ions (pH) may not maintain such a situation. Some insulin may precipitate in the actual presence of solid (i.e. in the classic maintained saturated solution) instead of maintain this tidy equilibrium. A change in the additive formulation may also provoke precipitation and thus reduce the driving force.

Where a drug in solid form is contained within a three dimensional matrix structure of a gel, the output is not linear and shows instead a relationship with the square root of time. This is classically described as the Higuchi relationship (Higuchi T, *Mechanism of sustained-action medication. Theoretical analysis of rate of release of solid drugs dispersed in solid matrices Journal of Pharmaceutical Sciences* Volume 52, Issue 12, pages 1145-1149, December 1963). Thus delivery (i.e. flux or dM/dt mass delivered per unit time) falls off slowly, because the diffusion path length that dissolved drug must take through the gel, becomes longer as the solid drug near the surface of the gel is progressively depleted.

However, in these systems, delivery rate is also a function of the rate-determining medium. In both the reservoir design and the matrix design, the rate determining medium is the analyte sensitive gel. As discussed above, the viscosity of the gel is not constant but changes in response to the concentration of the analyte. The changing viscosity of the gel has a much greater effect on the rate of delivery of the drug (by virtue of its effect on the diffusion coefficient, D) than the difference in delivery arising from how the drug is stored i.e. the influence of the matrix design vs the reservoir. The influence of the analyte sensitive gel effectively masks these underlying differences in delivery.

Thus, in both the matrix design and the reservoir design, a step wise operation can be expected and, when visualised on a graph of output vs time, the output of drug may be predicted to be a slanted set of analyte-triggered parallel steps based on the underlying relationship, although it is accepted that on and off stages might have some curvature (see FIG. 1). The output of drug from the matrix design is thus very similar to the output of drug from the reservoir design. The output from the matrix design in which the drug is present in solid form is also comparable to the output of drug by molecular diffusion from a reservoir through a gel membrane. Again, this is believed to be because of the influence of the analyte sensitive gel acting as a rate determining medium.

It will be appreciated that the gel could be adapted to control the rate of release of any solid drug contained therein based on the concentration of an analyte to which the gel is sensitive.

In the present invention, "drug" is intended to mean any active agent which has a desired therapeutic or prophylactic effect. The drug can be any drug which can be present as a solid and be contained within the three dimensional matrix structure of a gel of the invention. The solid form of the drug may have a crystalline structure or an amorphous structure. Preferably, the drug is water soluble. Preferably the drug is soluble in extracellular fluid. Preferably, dissolution of the drug is not a rate determining factor and is not pH dependent. In some embodiments, the drug has a physiological effect which brings about a change in concentration of the analyte when the gel is used in vivo. Preferably, the drug reduces the concentration of the analyte in vivo. This causes the gel to become more viscous and leads to reduced output of the drug from the gel i.e. a self-regulating negative feedback loop can be established. In one embodiment, the drug is an anti-hyperglycaemic drug such as insulin. Numerous forms of insulin are known to the skilled person, any of which may be used in the present invention. For example, human insulin or a semisynthetic analogue thereof may be used. Insulin analogs useful in the invention may be as described in "Insulin Analogs: Impact on treatment success, satisfaction, quality of Life and adherence", I Hartman, Clinical Medicine and Research Vol 6, number 2, 54-67 2008.

The gel of the invention comprises first and second gel-forming moieties which bind reversibly to one another to form a gel, wherein said binding is sensitive to the level of an analyte. The gel may be a reversible gel in which the interactive ligand pair (first and second moieties) are retained within the gel (i.e. their leach to the surroundings is prevented). In addition, phase separation of the components during the liquid stages of the gel-sol cycles is preferably prevented, thus ensuring the juxtaposition of the first and second moieties and increasing the life of the composition.

The first moiety preferably binds to the analyte and to the second moiety. In this way, the analyte will compete with the second moiety for binding to the first moiety. This will induce the transition from gel to sol as the bonds between the first and second gel forming moieties are broken. This in turn will reduce the viscosity and increase the permeability of the gel, allowing a drug contained within the gel to diffuse through the gel and be released from the gel at an increased rate.

The first and second moieties can be any moieties which can bind reversibly together to form a gel. It is preferred if the first moiety is a molecule which binds to at least part of the second moiety to bind the second moiety together, and the second moiety is a macromolecule which, when bound together, forms a gel. However, both the first and second moieties could contribute equally to gel formation. Preferably, the sensitivity of the gel to the level of said analyte arises because the first gel-forming moiety also binds to the analyte. Thus, the analyte competes with the second gel-forming moiety and, when the concentration of the analyte is sufficiently high, will prevent binding of the first and second gel-forming moieties, resulting in a decrease in the viscosity of the gel.

Bonding between the first and second moieties is caused by non-covalent forces such as hydrophobic, ionic, hydrogen bonding forces and the like. These interactions have been well studied in the art and their effects on molecular affinity and recognition are described, for example in Korolkovas et al, "Essentials of Medicinal Chemistry", pp 44-81 Wiley, 1976. Such reversible interactions are exemplified by the interaction between an enzyme and its substrate or a competitive inhibitor thereof; and antibody with its antigen, or a drug receptor site and its drug.

The first moiety may be any of a number of well-known entities which exhibit molecular recognition and reversible binding of micro- or macromolecules. The first moiety may be a natural binding protein, such as an antibody, an enzyme, a regulatory protein, a drug receptor site or the like. It is also possible to use synthetically modified binding molecules, such as chemically modified proteins. Such modified proteins sometimes have increased or decreased affinities for their substrates when compared to their natural unmodified counterparts. The first moiety may be a receptor built by imprinting and similar techniques (Andersson, *J Chromatogr B Biomed Sci Appl.* 2000 Aug. 4: 745(1):3-13; Bruggemann et al, *J Chromatogr A.* 2000 Aug. 11; 889(1-2):15-24; Haupt & Mosbach, *Trends Biotechnol* 1998 November; 16(11):468-75).

In some embodiments, the analyte is a carbohydrate, such as a sugar such as glucose. The first moiety may be, for example, an enzyme that binds the second moiety but that has been synthetically altered to remove its enzymatic activity. Alternatively, the first moiety may be a phenyl boronic acid polymer. However, it is preferred if the first moiety is a lectin. Lectins are carbohydrate-binding proteins of plants and animals with a wide variety of specificities for carbohydrates, (Lis et al, *Ann. Review of Biochemistry,* 42, 541 (1973); Goldstein & Hayes, *Adv. in Carbohydrate Chemistry and Biochemistry*, Vol. 35, Tipson and Horton, eds. (Academic Press, New York, 1978, pp. 128-341)). For example, ConA, a Jack Bean lectin, has specificity for α-D mannopyranose and α-D glucopyranose; soybean lectins are specific for α- and β-D-N-acetylgalactosamine and α-D-galactose units, and wheat germ lectin is specific for β-D-N-acetyl glucosamine. Other lectins that may be used include the pea (*Pisium sativum*) lectin and mannose binding protein. These binding pairs may form the first and second moieties of a gel useful in the invention. In a preferred embodiment, the first moiety is a lectin, and the second moiety is a gel-forming macromolecule which binds to the lectin, and which may be a carbohydrate polymer or polysaccharide, preferably containing glucose, fructose or mannose moieties. Examples include branched starches, dextrans, mannans, and levans, or synthetic carbohydrates such as ficoll-400, a synthetic polysucrose, and a synthetic polymer with pendant carbohydrate or sugar moieties. Preferably the first moiety is concanvalin A and the second moiety is dextran.

In one embodiment, blue dextran is used (Sigma) for the second moiety. Blue dextran is available in two molecular weights (40 K and 2 M), and comprises dextran covalently bonded to reactive blue. Each dextran molecule has many dye moieties bonded to it, and the molecule is blue and has free amine groups from the dye which are available for coupling. When coupling is done with blue dextran, the product is blue. This provides a qualitative and quantitative assessment of the success of coupling where the blue dextran has been bonded as a derivatised component to produce a polymer of conjugate for versions of the glucose sensitive system.

Some hormone-dependent tumours are treated with hormone antagonists like tamoxifen and cyproterone. The automatically-regulated delivery of such drugs in response to endogenous hormone peaks might offer an alternative to either their blanket use, which is strongly linked to toxic effects, or to the use of agents such as goserelin (which interfere with natural feedback in hormone biosynthesis and can paradoxically increase symptoms by doing so). Thus, a gel formed from testosterone and anti-testosterone antibody (Miyake, et al, *Chem Pharm Bull* 38 (4 1990): 951-5) could be used to deliver cyproterone for prostate cancer.

Another example is morphine and anti-morphine antibody (Kussie, et al, *J Immunol* 146 (12 1991): 4248-57) which could be used to deliver a morphine antagonist in response to influxes of exogenous morphine-like substances, such as heroin, in default of addiction therapy.

Either or both of the gel-forming moieties may be attached to cross-linked particulate entities such that the interstices between the entities allow gel-sol and sol-gel transformation and yet are not so small that the analyte cannot diffuse therethrough.

Preferred particulate entities are polymers which are locally cross-linked such that they form particles, sometimes known as "microgels", "minigels" or "fuzzballs", in which each particle is a discrete hydrogel structure which is substantially or completely surrounded by an aqueous interstitial region. It is preferred if the degree of cross-linking is greater than that in Carbopol 941, which has 1 linker for every 3300 monomers (Carnali & Naser, 1992, *Colloid Polymer Sci.* 270: 183-193).

In certain embodiments of the invention, the particulate entities have a mean diameter of 150 μm or 100 μm or less, preferably in the range of from 10 to 80 or 20 to 70 μm, as this may prevent the composition from crossing a membrane with pore sizes of 0.1 μm and above, and yet allows easy passage of the analyte and drug which have to pass through the composition.

There are a number of variations in which the first and second moieties can be attached to the particles. For example, the particles can have either the first or the second moieties attached (covalently or otherwise) directly thereto, or can have both the first and second moieties directly attached (covalently or otherwise) thereto. Alternatively or additionally, instead of being directly attached, the first and/or second moieties can be indirectly attached via a polymer. Suitable polymers are known to the skilled person and include acrylic backbone polymers, dextrans, celluloses and other sugar polymers. The first and second moieties can be attached to each other (e.g. in the manner described in WO95/01186) with one or other being directly or indirectly attached to the particles.

The first and second moieties may be provided in the form of a copolymer. This may be made by polymerising prepared derivatives of the first and second moieties. At its simplest, this can make a linear polymer bearing both moieties. Any type of polymer backbone produced by any relevant polymerisation technique is suitable for use in this embodiment. The copolymer may be a polymer backbone carrying the gel-forming moieties, and may be permanently cross-linked. In one embodiment, the methacrylate derivatives of the gel-forming moieties such as lectin and polysaccharide (for example, synthesised first from the raw lectin and polysaccharide, using a reaction with methacrylic anhydride) are polymerised to make an acrylic backbone polymer, carrying the gel forming moieties as pendants. It will be appreciated that any gel-forming moiety can be used in place of the lectin and polysaccharide.

Dextran is capable of methacrylate derivatisation (i.e. in the pre-polymerisation stage with methacrylic anhydride) at many points along its length, the number depending on conditions, since each hydroxyl group of every glucose unit in the dextran chain, is potentially susceptible to methacrylation. Accordingly, dextran moieties can permanently cross link the linear copolymer, producing a range of three-dimensional networks simply because it can start forming polymer chains at any point at which it has a methacrylate modification. Unless the degree of cross linking is very high, the ensuing products are likely to be flexible and gelatinous because of the length and mobility of dextran. Concanavalin A can also be multi-methacrylated, but because this molecule is globular, the product may be an aggregate and not a gel in which flexible networking extends throughout.

The fundamental character of products made by a polymerisation process such as the one described above is hydrophilic, but, in cases where the polymerisation product becomes too large and complicated to remain soluble, the product merely swells in water and does not form a solution (e.g. soft contact lenses are an example of a product made from a hydrogel that swells but does not dissolve). The permanent links dictate the major characteristics of the product in terms of its viscoelastic qualities, and so those products which have less derivatisation of the dextran and concanavalin A (for example) will be viscous liquids, while those which have extensive modification and thus allow complicated cross linking, will be solid hydrogels.

However, the interactive ligands are able to connect across the polymer chains non-covalently producing temporary bonding additional to any permanent bonds made during polymerisation. It is these which are crucial in terms of the reversible binding of the gel because, when in contact with the analyte, e.g. free glucose, the temporary bonds will be dismantled. When this happens, there will be a change in the properties of the product and it will become more permeable, as the notional pores throughout the lattice open up and leave only the permanent cross links. If the derivatisation and consequent permanent cross linking of the gel has been appropriately low, a viscous liquid can result when all of the permanent and temporary linking is in place. When the analyte is added, this liquid will lose viscosity and, because the reaction is reversible, this gel-sol change can be dependent on the concentration of analyte that has diffused into the gel.

Where the first and second gel-forming entities are not copolymerised, each component is multivalent in order that a three dimensional network or matrix results (and at least one component must have a valency greater than two, since two divalent interactants produce a linear arrangement).

In a gel comprising lectin and dextran which are not attached to one another or to other particles, the lectin is in its naturally tetravalent form which can dissociate into stable dimers at some pH values. These dimers are obviously smaller and are at a greater risk of loss from the gel. The combination of the tetravalent concanavalin A and the multivalent (branched) dextran produces a gel, which consists of a three dimensional network stabilised with only temporary bonds. However, the components can gradually leach away when in the sol state: phase separation may not be obvious but may contribute to progressive loss of action after several cycles.

However, when the interactive components are copolymerised or attached to particles, each component could be monovalent, and this would still form a gel, as essentially the conjugate becomes multivalent. Accordingly, certain gels described herein do not require first and second gel-forming moieties which are multivalent. In a preferred embodiment, lectin dimers (or tetramers stabilised by binding onto the framework) can be used. Dextran may be substituted with a variety of other glucose bearing entities, including simple pendant glucose. However, single pendant glucose may reduce the flexibility of the resulting gel and in fact, some permanent cross linking with dextran might be useful to give flexibility and prevent leaching away in the sol phase. The gel may be as described in WO 03/006993.

Preferably, the gel is formed in a substantially flat layer. Preferably, the thickness of the gel is no more than 5 mm. More preferably, the thickness of the gel is from about 1 mm to 4 mm inclusive. Even more preferably, the thickness of the gel is no more than 2 mm and is most preferably about 1 mm thick.

In a second aspect, the invention provides a method of manufacturing the gel of the first aspect of the invention, comprising either (i) adding a drug in solid form to a gel, or (ii) adding a drug in non-solid form to a gel and subsequently causing the drug to solidify, wherein the gel comprises first and second gel forming moieties which bind reversibly to one another to form a three dimensional matrix, said binding being sensitive to the level of an analyte.

In some embodiments, the drug is mixed into the gel so that it is substantially uniformly dispersed throughout the gel. Alternatively, the drug may be concentrated in particular regions of the gel, for example, the periphery or the core.

The drug may be solidified by precipitation or by any other suitable means including solvent evaporation.

When the drug is insulin, the concentration of insulin before it added to the gel may be at least about 15 mg/ml, more preferably at least about 20 mg/ml and most preferably at least about 25 mg/ml.

The isoelectric point (pI) of the drug may be used to determine the conditions under which the drug can be precipitated or under which the drug can be maintained in precipitated form. The pI is the pH at which the net charge of a molecule is zero and at which the molecule is least soluble. For example, the pI of native insulin is 5.4. However, in concentrated solutions, precipitation of insulin can be seen to begin at pH values higher than the pI because the solubility of insulin drops sharply below pH 8 (see Fischel-Ghodsian and Newton J; Drug Targeting (1993) 167).

It is possible to dissolve human insulin at 20 mg/mL with phenols and 10 mg/mL at pH 8 without phenols. Further-more, as discussed in Brange. J. (1987) *Galenics of Insulin: The Physico-Chemical and Pharmaceutical Aspects of Insulin and Insulin Preparations*, the higher the concentration of either zinc or insulin in a formulation, the less pH tolerant the solution is below 8. For example, insulin will precipitate at pH 7.4 if concentrated. Thus, in some embodiments, a drug such as insulin may be precipitated by altering the pH of the medium within which the drug is dissolved and/or by adding zinc.

Precipitation may be caused by adding one or more precipitants to the gel. The precipitant will be chosen according to the drug to be precipitated. Examples of precipitants include zinc and agents capable of altering the pH of the gel such as acids. As mentioned above, although the pI of insulin is 5.4, it is not necessary to lower the pH to 5.4 in order to precipitate insulin. When the drug is insulin, the pH of the gel may be lowered to no greater than about pH 7.9, pH 7.8, pH 7.7, pH 7.6, pH 7.5, pH 7.4, pH 7.3, pH 7.2 pH 7.1, pH 7.0 or less. Preferably, the pH is lowered to about pH 7.4.

Precipitation may also be induced by any other technique known in the art either alone or in combination with any other technique mentioned herein. For example, precipitation may be caused by increasing the concentration of the drug, increasing or decreasing the temperature of a solution within which the drug is dissolved, diluting a drug solution with a solvent in which the drug is insoluble or denaturing the drug. Alternatively or additionally, precipitation may be achieved by removing a solubility factor which keeps the drug in solution. The solubility factor may be any substance known to complex with the drug to affect or stabilise the solubility of the drug. For example, (and particularly if the drug is insulin) a phenol such as phenol, cresol or a related phenolic substance may be used. The solubility factor may be removed by any means, for example by passive diffusion or dialysis.

In a third aspect, the invention provides a drug delivery device comprising a container and the gel according to the first aspect of the invention, wherein the container is configured to maintain the gel in substantially flat layer and limit expansion of the gel caused by influx of water into the gel by osmosis.

Generally, the container may have a size and shape which is capable of containing a gel of the invention and limiting the expansion of the gel as it absorbs water by osmosis, thereby limiting or preventing dilution of the gel. It is important to limit expansion and dilution of the gel in order to preserve the path length of the gel (i.e. the distance through which the drug must travel in order to be released), the differentiation between the gel and sol states and the ability of the gel to switch between these states. The internal dimensions of the container will depend on the size and dimensions of the gel to be contained and the amount of expansion which is deemed to be acceptable. In one embodiment of the invention, the container is configured to be implanted into the body of a human or animal subject. In this case, the external dimensions of the container will be limited by the anatomy of the human or animal subject and the manner in which the agent is to be delivered.

When the drug delivery device is configured to deliver insulin in response to increased glucose levels, it is preferred if the device is located intraperitoneally because this allows glucose to reach the system quickly and for insulin to be released at a higher rate, than if, for example, the system was located subcutaneously. In addition, peritoneal fluid has a glucose level which mirrors blood glucose levels. That is not to say that the device cannot be used subcutaneously or even externally. The location should be selected so as to suit the condition to be treated or prevented and the drug to be released.

Preferred features of each aspect of the invention are as for each of the other aspects mutatis mutandis. The prior art documents mentioned herein are incorporated to the fullest extent permitted by law.

EXAMPLES

Example 1—Performance of an Insulin Delivery Device In Vivo

An experiment was designed to test the suitability of a closed loop glucose sensitive insulin delivery device in vivo. The insulin delivery device comprised a reservoir for insulin and a glucose responsive gel comprising con A and dextran which functions as a barrier to control the release of insulin from the reservoir. In normal levels of glucose, the gel is in a gel state and the rate of insulin release is limited. When the level of glucose increases, the gel becomes less viscous as its three dimensional structure is dismantled and the rate of insulin release is increased.

Glucose-Sensitive Gel Component

Briefly, using an aseptic process throughout, methacrylated derivatives of dextran RMM 500 kDa (D500) and concanavalin A, were dissolved in sterile water. The mixture was polymerised as a 60 µm thick layer between glass plates in the presence of the initiator Irgacure 2959® (0.178µ moles per 100 mg methacrylated derivative) to give a final content of both dextran and con A at 8.3% w/w, using uv irradiation at 365 nm, 10 mJ cm$^{-2}$ for 5 minutes and stored aseptically at 4° C. for at least 24 h before use. The gel was stirred thoroughly and spread as a thin layer between circular cellulose nitrate membranes of 0.05 µm pore size ready to incorporate into the device. When screwed down tightly, the polymer layer governs the output of insulin from the reservoir, forming a flat seal, resistant to osmotic effects because of rigid reinforcements to the confining cellulose membranes. The pore size of the latter is too large to retain individual con A and D500 molecules but does not allow the passage of the partially polymerised version. This membrane did not slow down the passage of insulin and was used in preference to a 100 kDa MWCO dialysis disk which impeded insulin diffusion. The path length of the gel was a variable set between 1-3 mm.

Method

The device was sutured in place in the peritoneal cavity and its refill circuit tunneled through the dorsal musculature.

Each end of the circuit was closed with a needle-accessible port and was sutured in place subcutaneously. A venous access port was place in a feed vein to the jugular for sampling and administration throughout the study. At surgery, the device had already been filled with saline and all implantable components had been hypochlorite-sterilized. The pig was allowed to recover and heal, was rendered diabetic with 2-3 iv low doses of streptozotocin until blood glucose levels were >20 mmol/L and then soluble insulin was introduced into the reservoir of the device.

Results and Discussion

Figure 1:
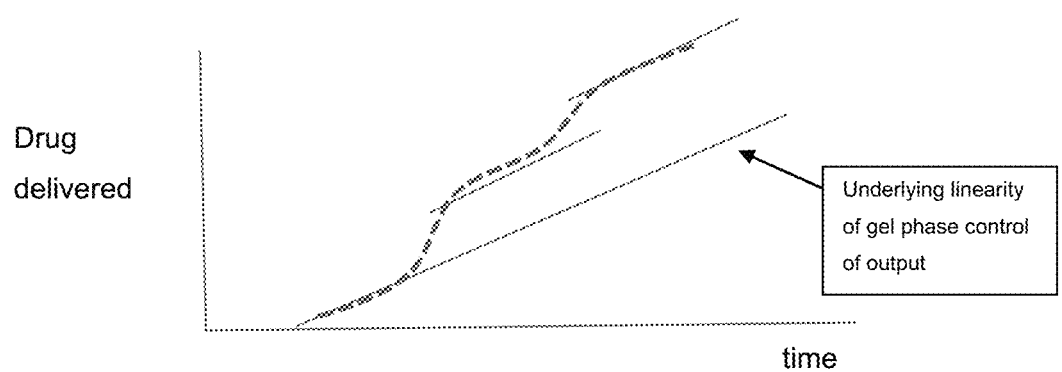
FIG. 1: Illustration of how analyte variation changes gradient of linear output.
Figure 2:
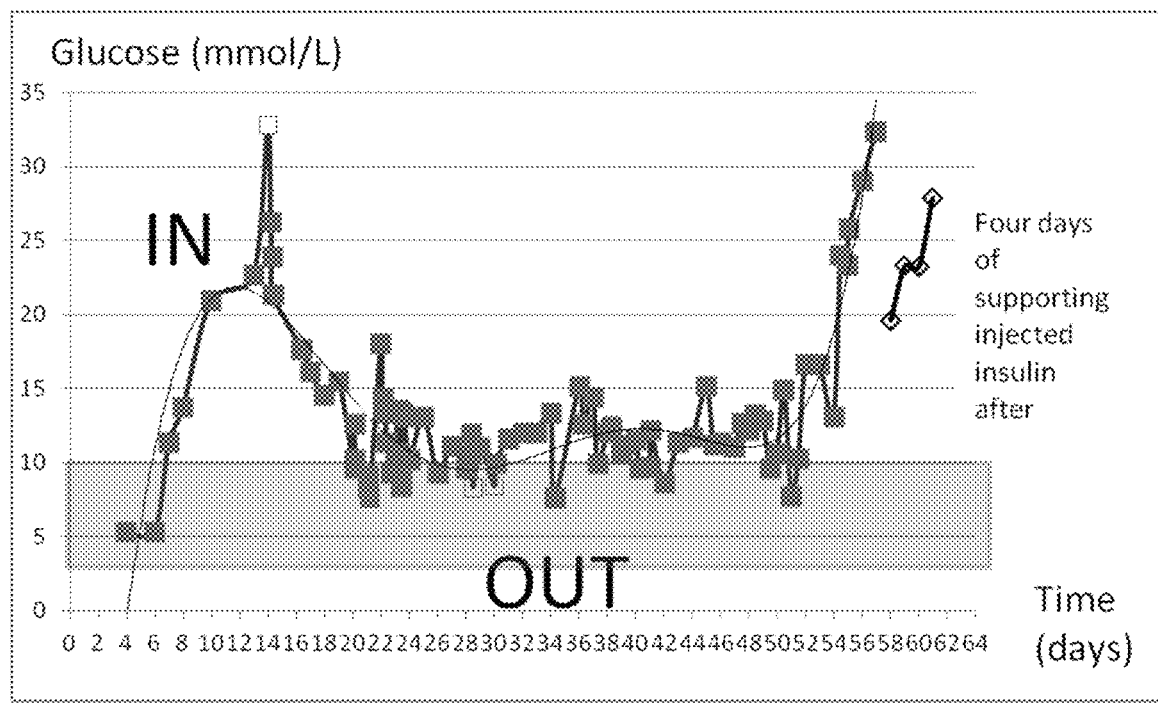
FIG. 2: Graph showing the blood glucose level of a diabetic pig over a period of 64 days. Filling, emptying and exhaustion states of an insulin delivery device are shown.
Figure 3:
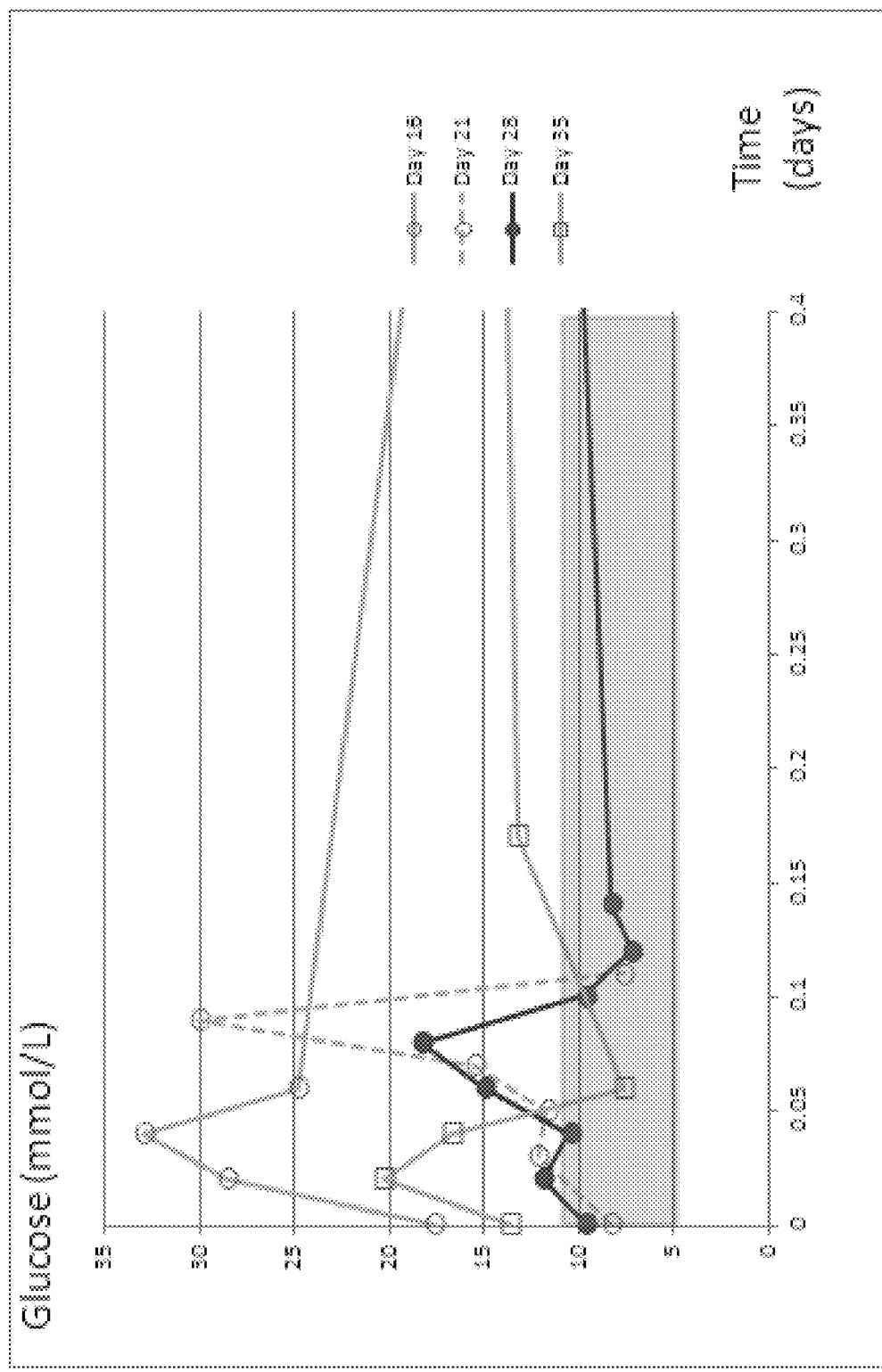
FIG. 3: Graph showing the change in blood glucose level of a pig following glucose challenges on four different days.

The blood glucose was reduced from diabetic levels to closer to normal range on day 22, about six days after introduction of the insulin into the device (day 16) (see FIG. 2). During this time, oral glucose tolerance tests were progressively better controlled, such that although peaking at up to 20 mmol/L, they returned to normal within 30 min (FIG. 3).

The pig was at no time hypoglycaemic and had normal access to food and water, even during glucose challenges, gaining weight and in good health. It had severe diabetes but was receiving optimum insulin with minimal excursions from the normal.

Insulin was removed from the device about 8 days after normoglycaemia was established but it was a further 24 days before the diabetic blood glucose levels were re-established (see FIG. 2). It should be noted that the device is designed to be refilled once insulin is depleted. Under normal circumstances, insulin would not be removed from the device and therefore an opportunity to observe the surprising outcome of this experiment would not arise with normal use of the device.

Assay by HPLC of the residual reservoir fluid for this pig after removing it (on day 30 by exchanging the reservoir insulin for saline using the refill circuit), revealed almost no insulin content. Initially this was a surprise since the BG was still clearly well controlled.

The conclusion was that the insulin from the reservoir must have migrated into the gel rather than equilibrating between the aqueous gel and the reservoir. A precipitate or crystallisation within the gel was suspected because a loss of solubility would occur if there was inadequate phenolic bactericide (lost by diffusion) to stabilise the insulin hexamer and especially if the pH equilibrated to peritoneal 7.4 from the formulated 7.8 where it would remain soluble. Being stored at 37° C. is also not optimal, although isoelectric loss of solubility may protect insulin from the protein fibrillation effects promoted at raised temperature. The insulin precipitation hypothesis was supported by the fact that the BG did not rise again for a further 24 days, the gel presumably holding enough solid phase insulin to maintain the mechanism despite the aqueous reservoir now comprising plain saline.

In the 14 days before the reservoir removal (including the 5.5 days reaching steady state), at least (14×150 U)=2100 U must have been delivered, leaving a maximum of 2900 U from the original fill in the 10 mL reservoir and the 2.5 mL gel (i.e. 12.5 mL). Had the gel simply equilibrated with the aqueous reservoir before removal, the concentration in the gel and the reservoir solution would therefore have been 2900/12=240 U/mL and thus the 2.5 mL gel would have held only 600 U. This could have maintained normoglycemia for only about 4 days, (on the basis of 150 U/24 h), whereas although the plot shows a very gradual loss of glycemic control before it finally becomes inadequate on day 52, reasonable suppression of hyperglycemia persisted a further 24 days after replacing the reservoir with saline.

The evidence implies that the reservoir and gel did not equilibrate but that the reservoir insulin deposited in the gel layer as solid, creating an overall, but probably not homogeneous depot of 2900 U in the 2.5 mL gel layer. This implies an average dose over the remaining 24 days of 120 U/day, presumably dropping from 150 to nearer 50 U/24 h and explains why control, including a glucose challenge on day 35, slowly deteriorated towards the point where glucose levels rose sharply. On dismantling the device, a residual white mottling in the otherwise clear gel was extracted and confirmed as insulin by HPLC. Clearly this interpretation has useful implications for safety and design, since an aqueous reservoir may not in fact be needed. The gel was still glucose-sensitive after explant.

Example 2—FITC-Insulin Assay

An assay was designed to investigate the precipitation of insulin in a glucose sensitive gel and monitor insulin release from the gel in response to glucose.

The object was to produce a suspension of fluorescent insulin (FITC-Insulin) in the gel by either exceeding the solubility of FITC-Insulin in the gel at pH 8, or making a high concentration of the FITC-Insulin in the gel at pH 8 and then dropping the pH to 7.4 (by adding minute volumes of acid) in the gel to try to precipitate it. This is the mechanism hypothesised to have been responsible for precipitation observed in Example 1. In that case, the pH change from 8 to 7.4 was not caused by adding acid as such, but by equilibration with peritoneal fluid across the semi-permeable membranes of the device. In addition, the insulin probably lost phenol by diffusion, an additional contribution to the loss of solubility.

FITC-Insulin was chosen for this work because it can be easily assayed by fluorimetry. FITC-Insulin is more quickly and extensively soluble at neutral than native insulin and solutions can be made quickly without the need for dissolving in acid and raising the pH to 8 (the method for native insulin). However, despite these differences, FITC-Insulin is both biologically active and otherwise quite similar to native insulin. For example, the pI of FITC-Insulin is 5.5 (Ye, S et al J Control Rel 112 (2006) 79-87) and thus very similar to the value of 5.4 for native insulin. As with native insulin, in concentrated solutions, the precipitation can be seen to begin at pH values higher than the pI because the solubility of insulin drops sharply below pH 8.

Figure 4:
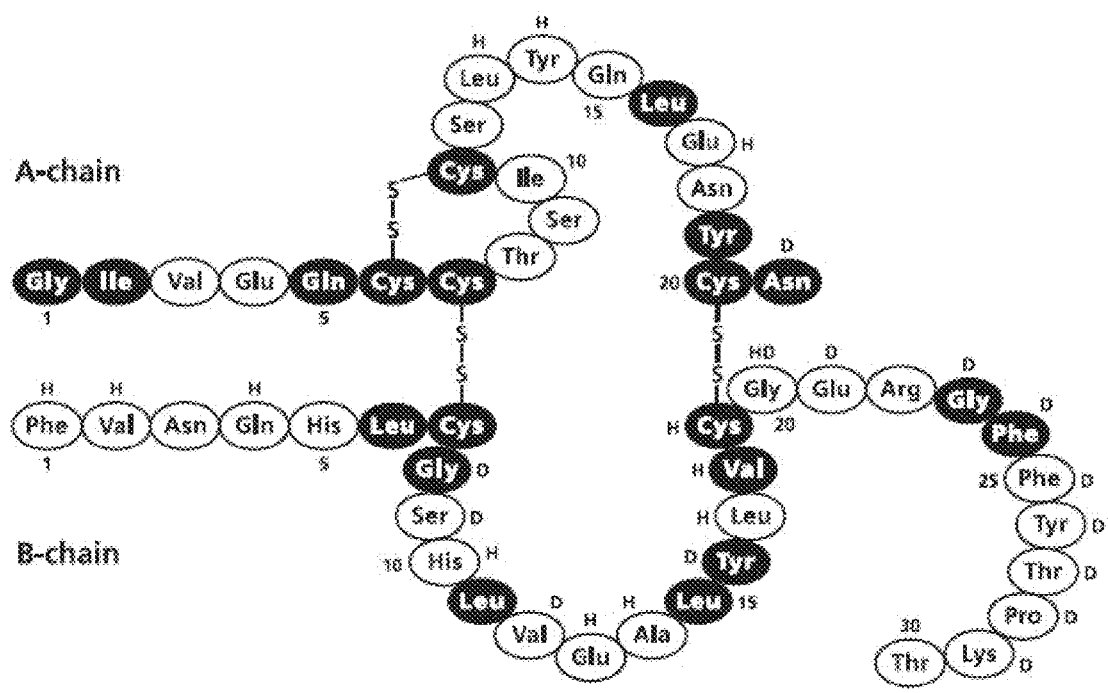
FIG. 4: Schematic drawing of an insulin molecule showing the available FITC tagging sites.

A plain mixture gel 10% con A: 10% D500 (preserved with sodium azide) was allowed two weeks to become completely transparent. FITC-Insulin was synthesised as a mono-labelled product using FITC resulting in tagging at the $A_1$ position on the A chain of human insulin using the Hentz method (see FIG. 4). This avoids the two other possible tagging sites $B_1$ and $B_{29}$.

Figure 5:
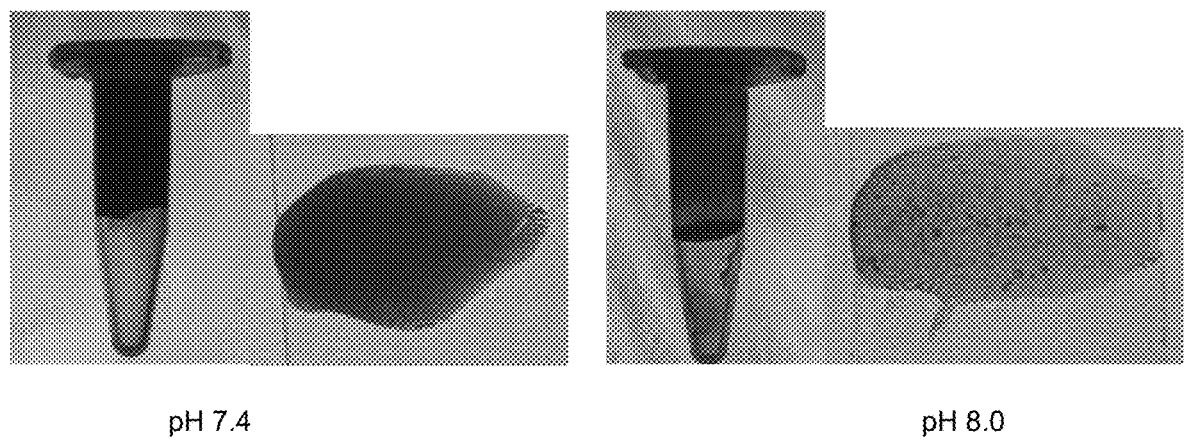
FIG. 5: Comparison of FITC-insulin at pH 7.4 where the insulin has precipitated and pH 8 where the insulin is dissolved in solution.

This $A_1$ product was then mixed into the gel at high concentration (25 mg/mL) at which concentration it is completely soluble at pH 8.0 (see FIG. 5). No phenol or zinc was present to raise or lower (respectively) the insulin solubility.

On addition of acid sufficient in small volume and concentration to produce pH 7.4, the FITC-Insulin precipitated in the gel, but could be re-dissolved on raising the pH back to 8.0. Native insulin behaves similarly in solution and the gel therefore makes no difference to this pH dependent solubility profile.

This is the most likely explanation for the extended delivery in the pig model described in Example 1 where the formulation at pH 8.0 was exposed to peritoneal pH (pH 7.4)

and the change allowed a precipitate to form in the gel layer, thus forming a depot that was slow to wash out and allowed the device to continue to work for two weeks after removal of the reservoir of insulin in solution.

Release Studies

A Perkin Elmer LS55 fluorimeter was used with 10 nm slit widths and the wavelengths set as follows: excitation wavelength 494 nm, emission wavelength 521 nm. A small lidded receptor vessel, stirred with a speed-controlled magnetic bar was set up with a tubing circuit to include a flow-through fluorimeter cell. The temperature was 20° C. The instrument was set to record fluorescence intensity on the time dependent channel at 0.1 minutes intervals (the max on this machine) up to 300 min (x-axis), with intensity set at arbitrary units 0-900 on y axis. Results were plotted on Excel 1 reading per minute (i.e. 1 in every 10 plotted).

As preliminaries, the FITC-Insulin was tested for efflux from dialysis tubing to determine the useful molecular weight cut off for the dialysis tube sacs for the experiment (i.e. to allow insulin to diffuse freely but to hold back the gel components). 50 k dalton tubing allowed only extremely slow transfer of insulin to the receptor fluid but with 300 k dalton and 1 Mega Dalton tubing, the receptor solutions were noticeably orange after 2 hours. The likelihood is that 36 k dalton insulin hexamers are present in the gel concentrate, despite no zinc or phenol to stabilise this form and that this makes diffusion slow through the smaller 50 k dalton pores.

The 1M dalton tubing was used to avoid transfer through the pores being rate limiting so that the difference between solution and suspension systems would be demonstrated in terms of delivery.

A sample of the dye-free gel in a section of tubing closed at each end with a tubing clip, swelled within 2 hours as water was drawn in by diffusion. Thus the gel because slightly diluted. During the same observation period, there was no cloudiness in the bulk fluid and thus little dextran (500 k) escaped under these circumstances, although there may have been some loss of Con A (not measured).

A small sample of the FITC-insulin in solution in the gel at pH 8 and a similar sample of FITC-insulin in suspension in the gel at pH 7.4 were each placed in a short length of dialysis tubing and clipped at each end. This was placed in the vessel once the flow through was working and a zero baseline established.

Figure 6:
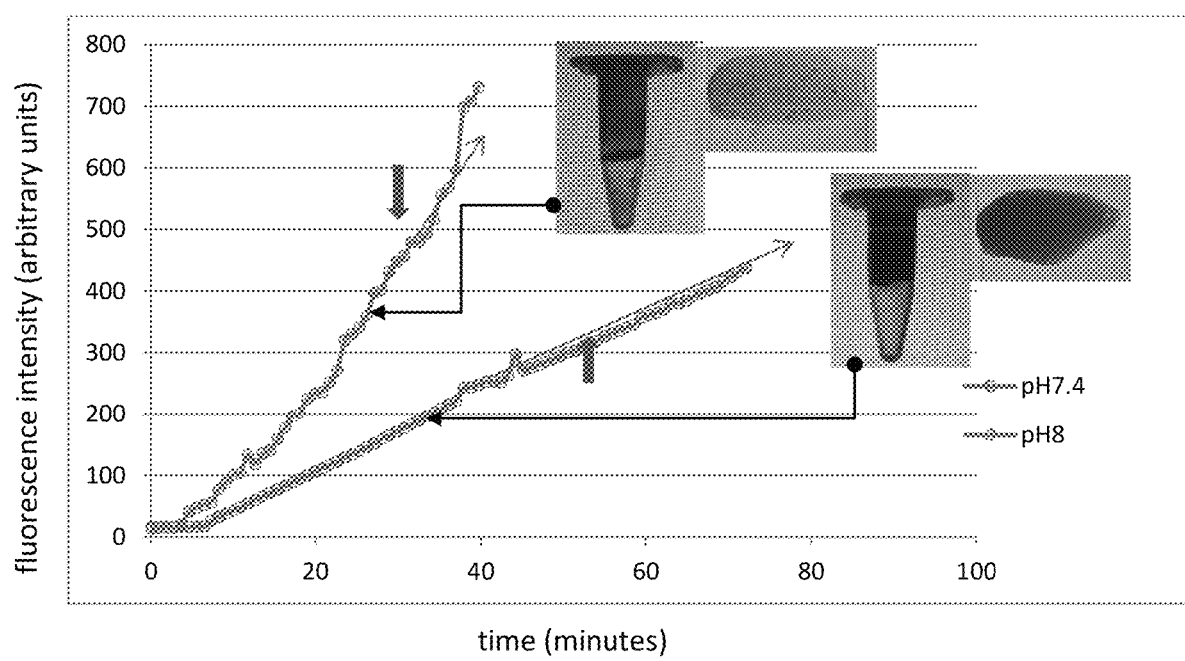
FIG. 6: Graph showing the output of FITC-insulin from a gel at pH 7.4 and at pH 8. The arrows show the point at which glucose was added.

The output results are shown in FIG. 6. The output of FITC-Insulin can be seen from the two systems. The output rate is greater from the solution than from the suspension. This is because the driving concentration is lower once some of the FITC-Insulin has been precipitated. The formation of a suspension still, however, allows efflux of FITC-Insulin in solution to continue and eventually all the precipitated FITC-Insulin will dissolve. In each case, most of the FITC-Insulin remained inside the dialysis sac and the plot was in practical terms a straight line, showing no signs of depletion.

The addition of glucose (at the solid arrows) does not in this case produce a very great change in rate. This is because the gel has become somewhat diluted by osmosis, this process not having been opposed by strategies to keep the gel in a confined volume (thus preserving) its concentration and responsiveness. To operate in this way, the gel should be in a custom built container holding the gel layer flat and unable to swell.

The invention claimed is:

1. A gel comprising first and second gel forming moieties which bind reversibly to one another to form a three dimensional matrix, said binding being sensitive to the level of an analyte, and a drug in the form of a solid contained in the three dimensional matrix, wherein the first gel forming moiety is concanavalin A or methacrylated concanavalin A and the second gel forming moiety is dextran or methacrylated dextran, and wherein the solid drug is in dynamic equilibrium with a dissolved form of the drug.

2. The gel of claim 1, wherein the solid is a precipitate.

3. The gel of claim 1, wherein the solid is substantially evenly dispersed throughout the three dimensional matrix.

4. The gel of claim 1, wherein the drug is insulin.

5. The gel of claim 1, wherein the first gel forming moiety is concanavalin A and the second gel forming moiety is dextran.

6. The gel of claim 1, wherein the analyte is glucose.

7. The gel of claim 1, wherein the gel is formed in a flat layer having a thickness of 1 mm or less than 1 mm.

8. A method of manufacturing the gel of claim 1, comprising either (i) adding the drug in solid form to a gel, or (ii) adding the drug in non-solid form to a gel and subsequently causing the drug to solidify.

9. The method of claim 8, wherein the drug is mixed into the gel so that it is substantially uniformly dispersed throughout the gel.

10. The method of claim 8, wherein the drug is solidified by precipitation.

11. The method of claim 10, wherein precipitation is caused by adding one or more precipitants.

12. The method of claim 11, wherein the one or more precipitants is selected from zinc and an acid.

13. The method of claim 12, wherein the precipitant is an acid and the addition of the acid lowers the pH of the gel to about pH 7.4.

14. The method of claim 8, wherein the drug is insulin and the concentration of insulin before it is added to the gel is at least 20 mg/ml.

15. A drug delivery device comprising a container and the gel according to claim 1, wherein the container is configured to maintain the gel in a substantially flat layer and limit expansion of the gel caused by influx of water into the gel by osmosis.

16. The gel of claim 1, wherein the first and second gel forming moieties are in the form of a copolymer, the copolymer comprising a polymer backbone bearing both the concanavalin A or the methacrylated concanavalin A and the dextran or the methacrylated dextran.

17. The gel of claim 16, wherein the first gel forming moiety is methacrylated concanavalin A and the second gel forming moiety is methacrylated dextran.

18. The gel of claim 16, wherein the copolymer is permanently crosslinked.

19. The gel of claim 1, wherein the second gel forming moiety is methacrylated dextran and/or wherein the first gel forming moiety is methacrylated concanavalin A.

20. The gel of claim 19, wherein the first gel forming moiety is methacrylated concanavalin A and the second gel forming moiety is methacrylated dextran.

21. A drug delivery system comprising the gel of claim 1, wherein the drug delivery system does not comprise a reservoir containing the drug.

22. The drug delivery system of claim 15, wherein the first and second gel forming moieties are in the form of a copolymer, the copolymer comprising a polymer backbone bearing both the concanavalin A or methacrylated concanavalin A and the dextran or methacrylated dextran.

23. The drug delivery system of claim 15, wherein the first gel forming moiety is methacrylated concanavalin A and/or the second gel forming moiety is methacrylated dextran.

24. The drug delivery system of claim 15, wherein first gel forming moiety is concanavalin A and the second gel forming moiety is dextran.

* * * * *